(12) United States Patent
McCann et al.

(10) Patent No.: US 7,798,323 B1
(45) Date of Patent: Sep. 21, 2010

(54) PORTABLE MEDICAL EMERGENCY EQUIPMENT PACK

(75) Inventors: Mike McCann, North Augusta, SC (US); Lynn Piacentini, Glastonbury, CT (US)

(73) Assignee: DHS Systems LLC, Orangeburg, NY (US)

(*) Notice: Subject to any disclaimer, the term of this patent is extended or adjusted under 35 U.S.C. 154(b) by 0 days.

(21) Appl. No.: 12/456,688

(22) Filed: Jun. 19, 2009

(51) Int. Cl.
B65D 83/10 (2006.01)
(52) U.S. Cl. .................... 206/370; 206/570; 206/438
(58) Field of Classification Search ............. 206/370, 206/570, 225, 578, 569, 803, 214, 549, 736, 206/774, 577, 363–366, 367, 315.1; D3/290; 150/52, 113; 190/107, 901, 109, 110; 224/583; 383/11, 4, 26, 27, 86.1, 103, 38–40
See application file for complete search history.

(56) References Cited

U.S. PATENT DOCUMENTS

| | | | |
|---|---|---|---|
| 2,324,194 A | 7/1943 | Campiglia | |
| 2,359,372 A | 10/1944 | Leader | |
| 4,169,550 A * | 10/1979 | Williams | 224/633 |
| 4,386,642 A * | 6/1983 | Durbin | 190/110 |
| 4,513,866 A * | 4/1985 | Thomas | 206/570 |
| 4,585,127 A | 4/1986 | Benedict | |
| 4,609,084 A * | 9/1986 | Thomas | 190/110 |
| 5,207,303 A | 5/1993 | Oswalt | |
| D340,573 S | 10/1993 | Badeau | |
| 5,265,782 A | 11/1993 | McNamara | |
| D367,359 S | 2/1996 | Smith | |
| 5,533,534 A | 7/1996 | Cariello | |
| 5,865,314 A * | 2/1999 | Jacober | 206/570 |
| 6,000,509 A * | 12/1999 | Chisholm | 190/109 |
| 6,193,034 B1 * | 2/2001 | Fournier | 190/107 |
| 6,244,400 B1 * | 6/2001 | Bowers | 190/110 |
| 6,334,519 B1 * | 1/2002 | Tong | 190/107 |
| 6,343,694 B1 | 2/2002 | Parnell | |
| 6,484,912 B2 * | 11/2002 | Jones | 224/153 |
| 7,600,619 B2 * | 10/2009 | Sapyta | 190/107 |
| 2002/0114539 A1 | 8/2002 | Strevey | |
| 2005/0016808 A1 * | 1/2005 | Sapyta | 190/107 |
| 2007/0119883 A1 | 5/2007 | Albritton | |

* cited by examiner

Primary Examiner—Mickey Yu
Assistant Examiner—Rafael Ortiz
(74) Attorney, Agent, or Firm—Thomas A. Beck

(57) ABSTRACT

A foldable carrying medical pack made of flexible material, adapted to store medical emergency supplies and equipment. Clear storage pouches which contain the medical supplies and equipment are attached by Velcro, for easy removal, to the interior side of the medical pack. This arrangement allows for immediate visible access to every item stored in each pouch/compartment. Each pouch has a clear sewn-in compartment in the front of same, to insert labels therein providing a list of the contents. The label is inserted in the compartment to allow the contents of the pouch to be easily determined. The removable pouches can be replaced with additional pouches that contain medical supplies or equipment oriented toward a variety of different medical emergencies.

8 Claims, 8 Drawing Sheets

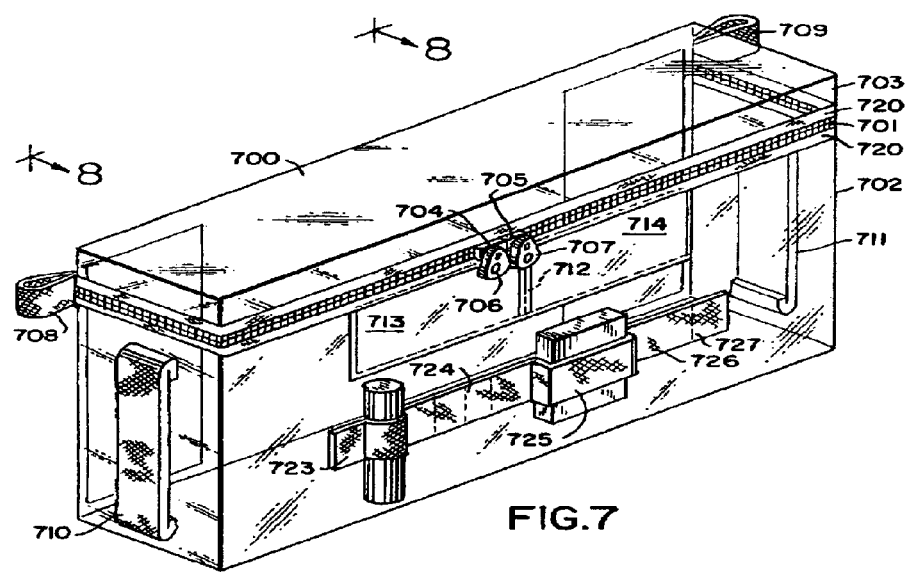
FIG. 7
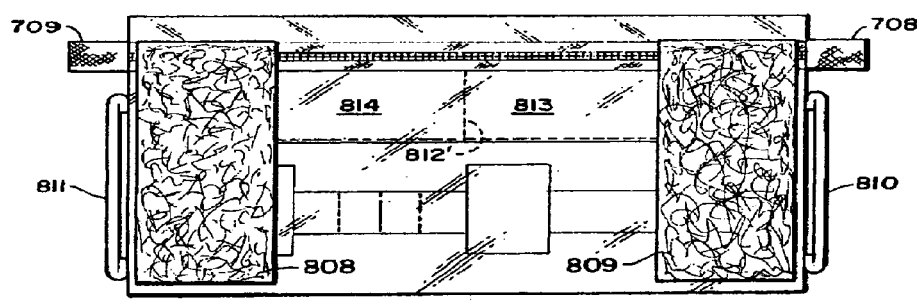
FIG. 8
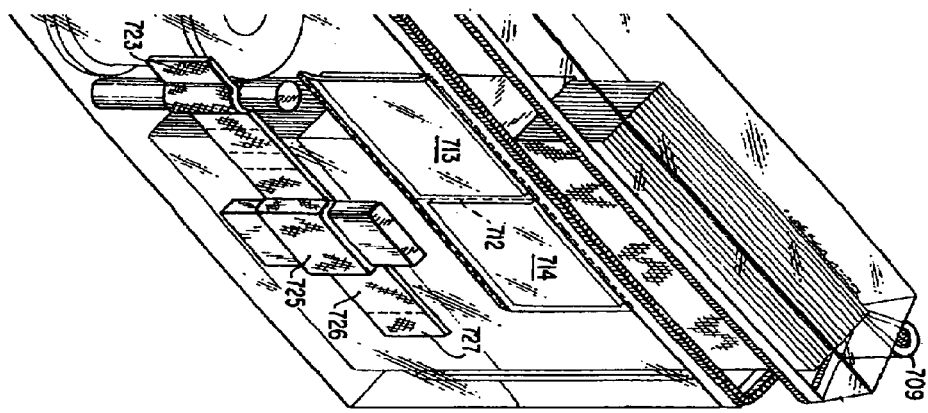

PORTABLE MEDICAL EMERGENCY EQUIPMENT PACK

FIELD OF THE INVENTION

The present invention relates to a foldable pack adapted to store of supplies and equipment. The foldable pack has an exterior side and an interior side. Clear storage pouches/compartments suitable for storing the equipment are attached by Velcro strips for easy removal to the interior side of the pack. This arrangement allows for immediate visible access to every item each pouch/compartment.

More specifically, the present invention relates to a pack adapted to store medical emergency supplies and equipment in a medical pack. Clear storage pouches which contain the medical supplies are attached by Velcro, for easy removal, to the interior side of the medical pack. This arrangement allows for immediate visible access to every item each pouch/compartment. Each pouch has a clear sewn-in compartment in the front of same, to insert labels therein providing a list of the contents. The label is inserted in the compartment to allow the contents of the pouch to be easily determined. The removable pouches can be replaced with additional pouches that contain medical supplies or equipment oriented toward a variety of different medical emergencies.

DESCRIPTION OF THE PRIOR ART

Medical response teams react to major as well as minor incidents in a variety of ways. Regardless of whether they respond with an incident command post or rapid deployable medical treatment system, the need for medical supplies oriented for specific incidents must be readily accessible. General supplies are carried in medical kits or cases. It is important that the medical emergency kits brought to medical incident sites are light weight enough to be quickly transported and color coded for mission orientation. It is imperative that kits contain a complete line of medical supplies that meet the needs of the responder to specific types of medical emergencies A portable medical equipment pack is disclosed in U.S. Pat. No. 6,343,694 in which storage pouches are stored in layers in a suitcase style pack. This system is comprised individual single cell modules that are stand-alone or used as a system and pockets are not capable of being rearranged. The pack does not fold in half sealed by Velcro but rathe has zipper means to close it up. The pack is designed as a backpack or to hang on a specially designed rack. This pack does not have the combination of individual elements embodied in the present invention.

A medical emergency kit disclosed in U.S. Pat. No. 5,207,303 in which storage pouches are stored in layers in a suitcase style backpack with carrying handles. This system is comprised individual single cell modules that are designed to flip open and pockets are also not capable of being rearranged. This pack does not have the combination of individual elements embodied in the present invention.

A survival backpack is disclosed in U.S. Pat. No. 6,484,912 which is essentially a backpack with a plurality of straps arranged to carry survival equipment that can be converted into a stretcher. This pack does not have the combination of individual elements embodied in the present invention.

A portable medical equipment pack is disclosed in U.S. Pat. No. 4,513,866 and U.S. Pat. No. 4,609,084 in which storage pouches are stored in layers in a suitcase style pack. This system is comprised individual pockets and drawer pockets that flip open and are not re-arraignable. The pack does not fold in half sealed by Velcro but zips closed. The pack is designed as a backpack that is self-supported with carrying handles. This pack does not have the combination of individual elements embodied in the present invention.

A portable medical equipment pack is disclosed in U.S. Pat. No. 340,573 in which storage pouches are stored in layers in a suitcase style pack. This system is comprised individual single cell modules that are stand-alone or used as a system and pockets are not re-arraignable. This pack does not have the combination of individual elements embodied in the present invention.

SUMMARY OF THE INVENTION

It is an object of the present invention to provide compact, efficient, visible and lightweight storage of a complete line of medical emergency supplies in a medical equipment pack. Storage in the carrying case is attained by open placement of removable storage pouches which are attached and secured in place by any suitable fastening means along the open interior face of the carrying case.

It is a further object of the present invention to allow quick, simultaneous and visible access to every item in the medical equipment pack. This is achieved by pulling apart the velcroed edges which secure the folded in half medical equipment pack, opening the pack flat out and having the storage pouches accessible to view or to remove from the carrying case. When the medical equipment storage pack is in its opened position, (i.e., unfolded or flat), all of the contents of the carrying case and the storage pouches are at once visible and readily accessible.

It is a further object of the present invention that in the event of multiple casualties at the emergency scene the medical supplies may be used by more than one provider at locations remote from each other. To achieve this, individual storage pouches are easily and readily detachable from the carrying case. Thus more than one paramedic may have ready access to the supplies contained within the medical equipment storage pack.

Accordingly, another object achieved by this invention is to have means to identify, store and access medical emergency supplies using a color coded carrying pack. This gives the provider the ability to arrange each medical pack providing maximum visibility and colored coded accessibility of the stored items. Multi-compartment zippered and detachable pouches are attached to the inside of the carrying case and these pouches may be quickly removed form the carrying case so that specific needed supplies can be in the hands of the provider who cannot be next to the carrying case. The pouches are transparent on all sides and have a label pocket so that the contents can easily and quickly be identified though still attached to the carrying case.

BRIEF DESCRIPTION OF THE DRAWINGS

The above features and advantages of the present invention will become more apparent by describing in detail preferred embodiments thereof with reference to the attached drawings in which:

FIG. 7 is an orthogonal view of one of the larger pouches contained within the interior of the portable medical equipment pack of the present invention.

FIG. 8 is a rear view of the larger pouch depicted in FIG. 7.

DETAILED DESCRIPTION OF THE INVENTION

Figure 1:
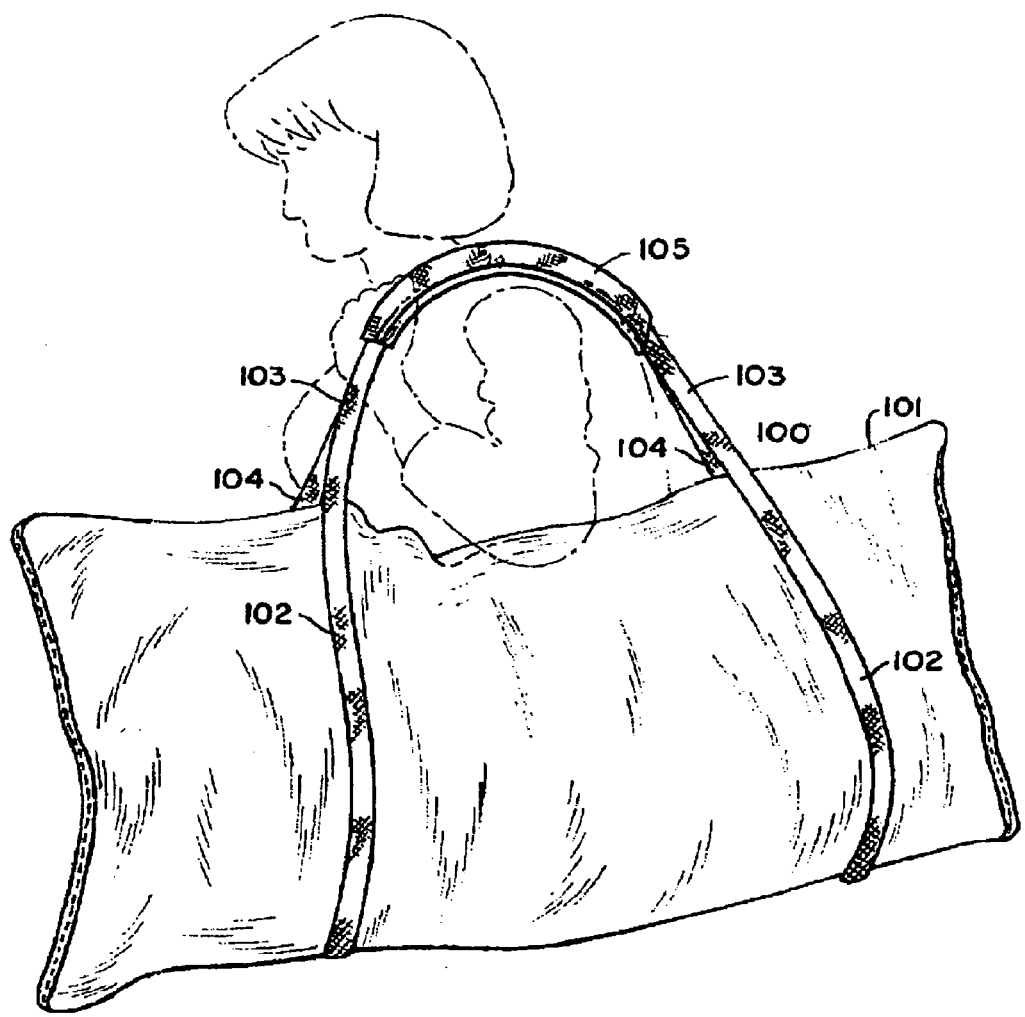
FIG. 1 is a side view of the portable medical equipment pack of the present invention in use with carrying straps.

Referring to FIG. 1, the portable medical equipment pack 100 is shown in its portable state folded over on itself, so only half of the exterior surface 101 of portable medical equipment pack 100 is viewable. A continuous support strap 102 is formed from a single band of web material, cotton, polyester or other suitable material that will not creep under a tension load, and is stitched to the exterior surface 101 of portable medical equipment pack 100.

The continuous support strap 102 as depicted in FIG. 1 as secured to the exterior surface 101 of the portable medical equipment pack is a closed curve resembling the shape of a hyperbolic paraboloid with the lower periphery portion of the hyperbolic paraboloid form folded inward and secured to the exterior surface of the portable medical equipment pack serving as supportive means for the portable medical equipment pack, and the raised peripheral portion of the hyperbolic paraboloid form serving as handle/carrying means for the portable medical equipment pack. More specifically, support straps 102 provide means for supporting the underside of the exterior surface of portable medical equipment pack 100 when it is being carried.

Carrying handle strap 103 is that portion of the continuous support strap 102 which is not secured to exterior surface 101. The continuous support strap 102 is made from a flexible web material and comprises two straps sewn onto the exterior of surface 101 at 102. These two straps 102 are spaced apart and parallel to each other and extend the length of the surface of the sheet of the portable medical equipment pack. Handles 103 are the ends of the continuous strap and extend beyond each end of the portable medical equipment pack. Handle 103 forms a semi-ellipse. There are two carrying handle straps, however the second carrying handle strap is barely visible in FIG. 1 at 104 behind carrying strap 103.

At each end of strap handle 104 and handle 103, both of which are extensions of continuous support strap 102, an insulated Velcro-containing handle wrap 105 is secured to handle 104. Handle wrap 105 provides insulation to the hand or hands if the pack is being carried by hand, or on the shoulder, so that the weight of the pack in use is diffused, and the width of the straps do not stress the fingers or shoulder carrying the pack.

Thus one edge of the handle wrap 105 is secured to end point of strap 104, and when it is desired to fold up the medical equipment pack for transporting same, handle wrap 103 is placed in contact with the handle wrap 104 within the interior of handle wrap 105 and the exterior side of the handle wrap 105 containing the Velcro is wrapped over on itself so that handle straps 103 and 104 are enclosed within Velcro handle wrap 105.

FIG. 1 shows one embodiment wherein portable medical equipment pack 101 is carried over the shoulder. As depicted, the handle wrap 105 provides insulation so that the weight of the portable medical equipment pack is dispersed over the area in contact with the shoulder thereby eliminating the narrow stress channel caused by the straps that would be absorbed by the shoulder if the insulated handle wrap were not present.

FIG. 1 shows the portability of the medical emergency pack. It can be stored fully stocked and supplied in any convenient location and can be quickly accessed when an emergency situation arises, without the need to gather supplies necessary to handle the emergency.

Figure 2:
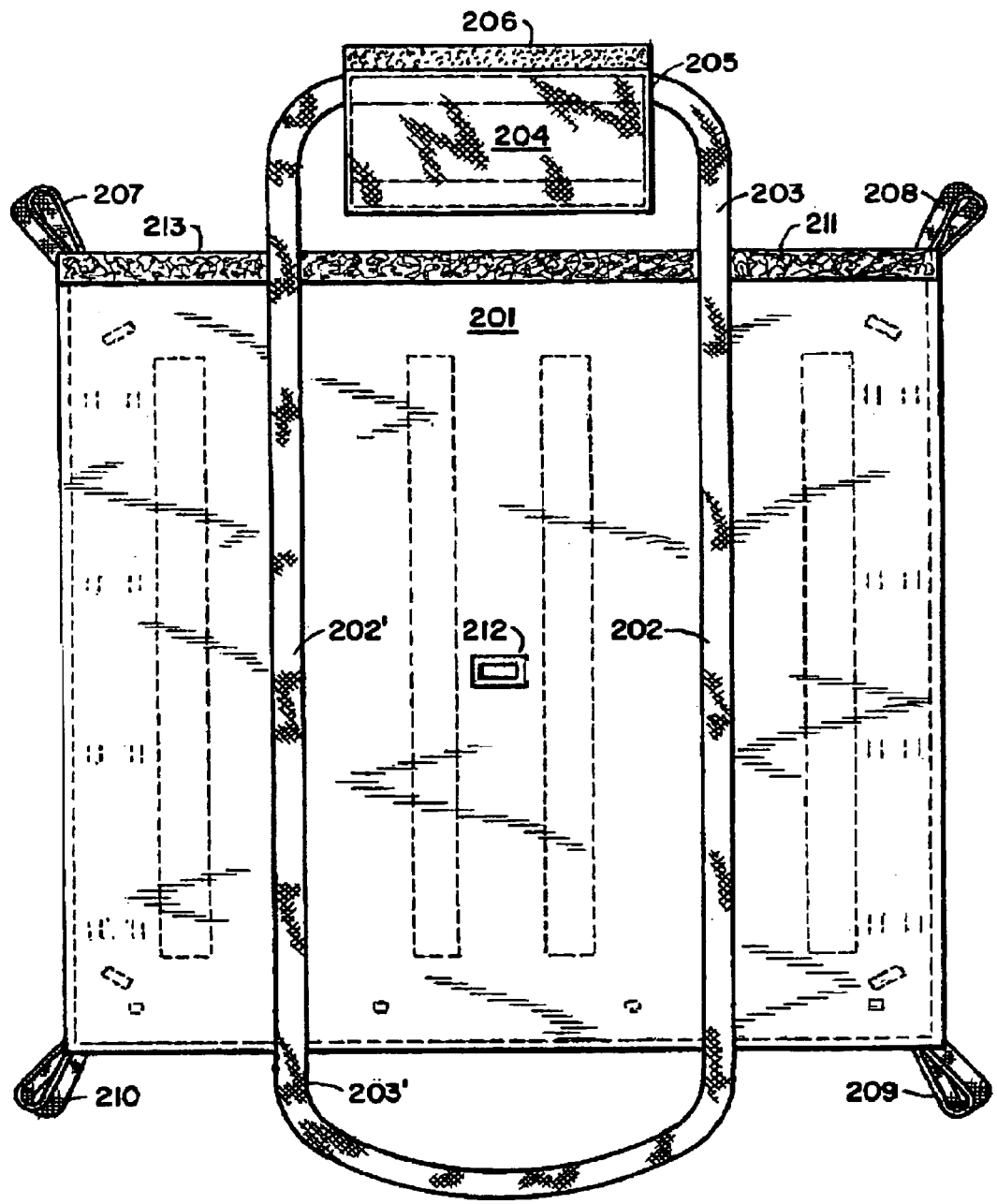
FIG. 2 is a top view of the exterior surface of the portable medical equipment pack of the present invention.

FIG. 2 depicts the exterior of the portable medical equipment pack 201 spread out flat. Continuous strap depicted as 202 and 202' is a single unitary piece since it has no beginning portion and no end portion, although it is designated in FIG. 2 as 202 and 202' for the sake of description. Parallel straps 202 and 202' are sewn into the material forming the portable medical equipment pack. Said straps serve to support the unit when the portable medical equipment pack is folded over on itself, (i.e. in half) as depicted in FIG. 1. The portion of the continuous straps 202 and 202' which extend beyond the surface of the portable medical equipment pack, to which straps 202 and 202' are attached, form flexible carrying handles 203 and 203' which are located at opposite circuitous ends of continuous strap forming 202 and 202'.

A soft handle rectangular wrap 204 having Velcro elements on opposite sides of same is secured by stitching means or any other suitable means to strap 203 at end 205. Handle wrap 204 is suitable for enclosing the continuous strap 203' located at the opposite end of the medical emergency pack, and doubling over on itself so that the hook section 206 of the Velcro surface is contacted with a loop section (not shown) on the reverse side of handle wrap 204, and a tubular-like handle is formed containing the ends of the two straps 203 and 203' within its interior when the portable medical equipment pack is folded over on itself, (i.e. in half) as depicted in FIG. 1. The rectangular handle wrap 204 is rolled over on itself containing the carrying handle straps within.

The sheet material forming the matrix or body of the portable medical equipment pack 201 used in accordance with the present invention is formed from any synthetic or natural polymer that: resists degradation from sun, ozone and weather; is not adversely affected if in contact with acids, alkalis, organic solvents, oils and assorted chemicals that are insidious to plastics; remains functional and useful over a wide temperature range; and displays outstanding physical toughness; resists burning; and has outstanding resistance to damage caused by flexing and twisting.

In the preferred embodiment of the present invention, the sheet comprises CORDURA®, which is a registered name of a high-performance Nylon 66 product manufactured by INVISTA. Although CORDURA is preferred, other polymeric materials having the properties mentioned above, such as a vinyl plastic, can be used.

The present invention uses as its preferred embodiment hook-and-loop fasteners to secure its various components together. The hook-and-loop fasteners consist of two layers: a "hook" side, which is a piece of fabric covered with tiny hooks, and a "loop" side, which is covered with even smaller and "hairier" loops. When the two sides are pressed together, the hooks catch in the loops and hold the pieces together. When the layers are separated, the strips make a characteristic "ripping" sound. A commonly used fabric fastener is Velcro® which is a brand name of the fabric. There are many other brands available besides Velcro, such as, for example, Aplix® brand, and an in-house brand made by WBC Industries.

The fibers most commonly used now to make Velcro are nylon or polyester. Velcro made of Teflon loops, polyester hooks, and glass backing has also been used. Generic terminology for these fasteners includes "hook and loop", "burr" and "touch" fasteners.

For the sake of discussion in this specification the fabric referred to in a preferred embodiment is Velcro, but this is by way of illustration only, and any hook-and-loop fasteners to secure components together according to the present invention can be used as well as other fastening means such as caps and eyelets or studs and sockets. Thus the invention is not limited to the preferred embodiment using Velcro as the fastening means.

Loops 207, 208, 209, 210 are located and extend diagonally outward at a 45° angle from each apex of the corners of said sheet. These loops are designed to allow the portable medical equipment pack be suspended from a vertical or quasi-vertical surface when in use at the site of an emergency.

In FIG. 2, extending horizontally along the entire top edge 213 of the portable medical equipment pack 201, there is a strip of Velcro loops 211 which strip connects with a strip of Velcro hooks (not shown) located along a horizontal edge of the interior of the portable medical equipment pack, which, when the portable medical equipment pack is folded over on itself, forms the transportable unit depicted in FIG. 1. The elements (i.e. hooks or loops) comprising these two strips of Velcro can be reversed if desired.

Figure 4:
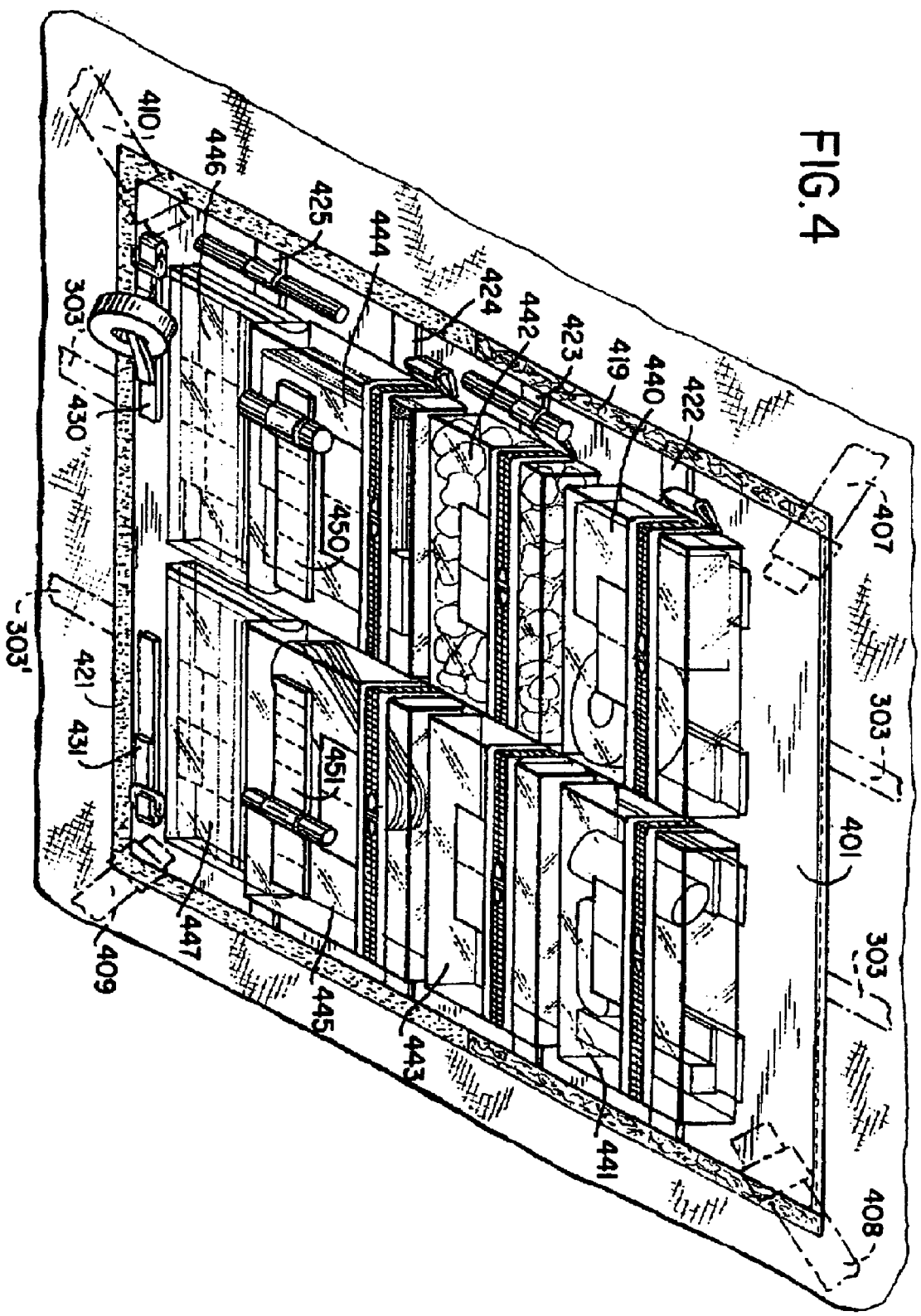
FIG. 4 is an oblique view of the portable medical equipment pack of the present invention suspended on the interior wall of a deployable shelter.

In the center of the portable medical equipment pack is a grommet 212. This grommet provides an opening which allows the portable medical equipment pack to be secured in its center to an interior wall which is not vertical but rather is arcuate or angular. This positioning of the portable medical equipment pack in use is depicted in FIG. 4.

Figure 3:
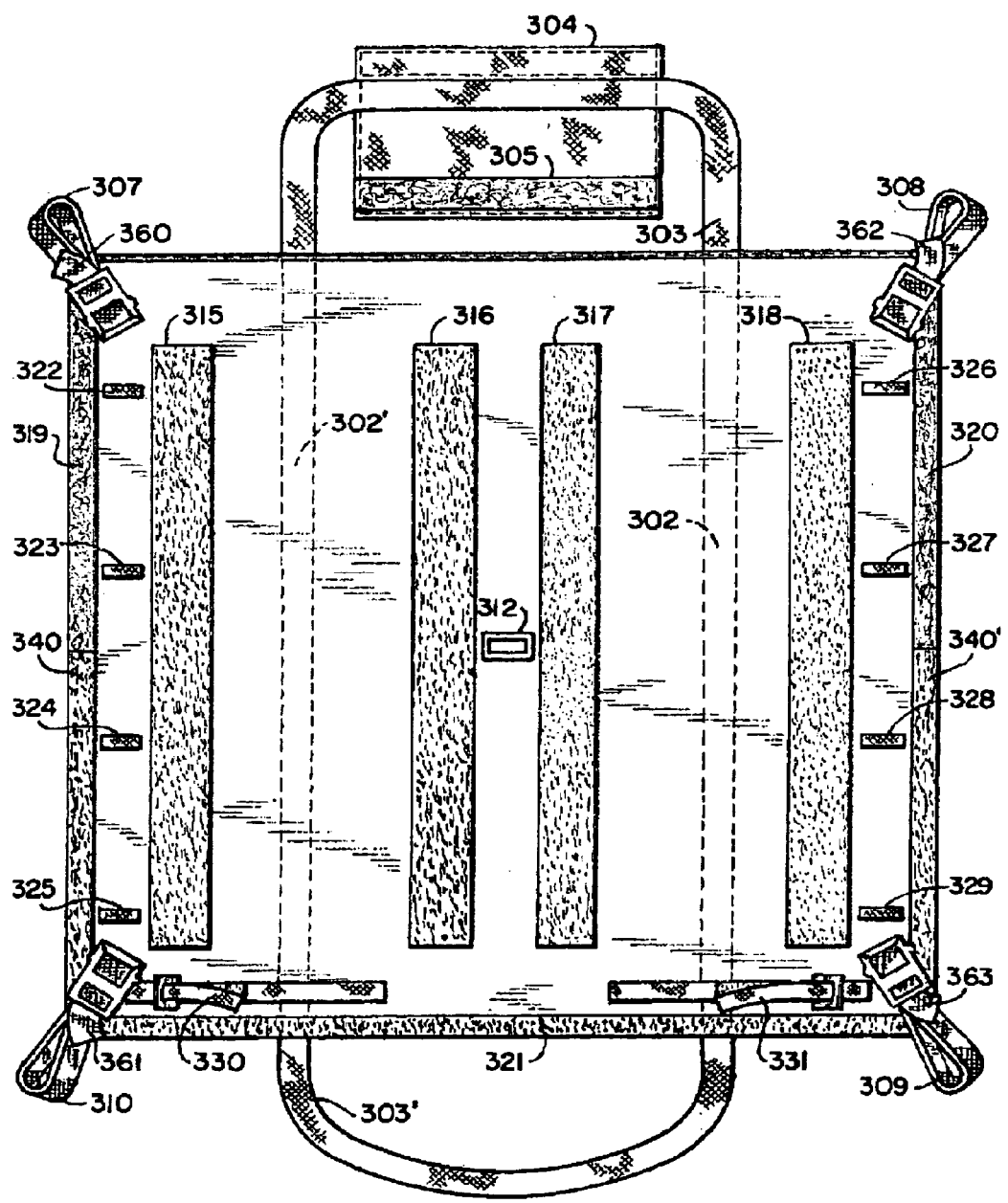
FIG. 3 is a top view of the interior surface of the portable medical equipment pack of the present invention.

FIG. 3 depicts the interior of the portable medical equipment pack 301 spread out flat without the pouches present which form an integral part of the invention. FIG. 3 depicts the reverse side of the portable medical equipment pack depicted in FIG. 2. FIG. 3 presents only the static elements of the invention, since the elements depicted are fixed in place, and thus are not removable.

Carrying handles 303 and 303' and handle wrap 304 are the same element as described in the description relating to FIG. 2 above. When the portable medical equipment pack is folded over on itself, handle wrap 304 containing Velcro surface 305 envelopes carrying straps 303 and 303', and Velcro strip 305 (either hook or loop) attaches itself to the antithetical Velcro strip located on the opposite side of handle wrap 304 (not shown).

There are four strips of Velcro 315, 316, 317 and 318 which extend vertically as depicted in FIG. 3, side by side, parallel to each other and to the direction of the supports straps 302 and 302' depicted in dotted lines, the dotted lines thus indicating that the straps are on the exterior of the portable medical equipment pack.

Two side edges 319 and 320 of the portable medical equipment pack possess Velcro strips. Along the entire length of each of these strips 319 and 320, the half-way point 340 and 340' of said length marks a change in the layer of Velcro used from hook to loop. From end 360 to midpoint 340, the Velcro strip can be a hook and from midpoint 340 to bottom 361, the Velcro strip along the length can be a loop. Similarly, from end 362 to midpoint 340', the Velcro strip is a hook and from midpoint 340 to bottom 363, the Velcro strip along the length is a loop.

When the portable medical equipment pack is folded over on itself for portability, the Velcro portions along 319 between 360 and 361 and along 320 between 362 and 363 join together, and the vertical sides of the portable medical equipment pack are sealed off and secure.

On a first side of the portable medical equipment pack adjacent to and in between Velcro strip 319 on the edge and Velcro strip 315, there is a column of expandable elastic loops 322, 323, 324 and 325; and on a second opposite side, adjacent to and in between Velcro strip 320 on the edge and Velcro strip 318, there is a column of expandable elastic loops 326, 327, 328 and 329. The expandable elastic loops, secured to the sheet material, are adapted to hold and secure elongated cylindrical, tubular items such as chest tubes, ET catheters, pens, trauma shears, etc.

Located and extending diagonally inward at a 45° angle from each apex of the corners of the interior side of the portable medical equipment pack are assemblies 307, 308, 309 and 310, each comprising a quick-release buckle and a strip of a web-like material which, when said elements are connected, forms an adjustable continuous loop. The strip of web material is adjustable at the buckle so various lengths are possible for each assembly. As noted above, these assemblies are designed to be secured to a wall or any suitable horizontal or vertical surface to allow the portable medical equipment pack to be suspended therefrom when in use at the site of an emergency.

Assemblies referred to above containing the web material and quick-release buckle, and suitable for use in the present invention are those described and disclosed in U.S. Pat. Nos. 4,150,464 and 4,171,555, the contents of which are incorporated by reference herein.

The quick-release buckle comprises separable cooperating receptacle and clasp members. The receptacle member includes a pair of locking slots formed in opposing sides thereof. The clasp member includes a pair of resilient arms having locking tabs thereon for releasably engaging the locking slots of the receptacle member. The receptacle member also includes a pair of grooves for slideably engaging cooperating raised ridges formed on a central arm of the clasp member for guiding said clasp member during insertion into and removal from the receptacle member. The central arm of the clasp member includes a pair of laterally extending edges for defining a limit to the inward bending of the resilient arms. The receptacle includes a belt end termination member including a slide member for adjusting the length of a belt looped around said slide member. The clasp member also includes a base member joining the three arms thereof and including a through slot for terminating a belt end or the like.

A useful embodiment of how the quick-release buckle of the portable medical equipment pack of the present invention is used, is shown in FIG. 4, which depicts the quick-release buckle attached at an angle to a wall of a deployable shelter.

At the bottom of matrix sheet 301, and parallel to Velcro strip 321 that extends along the bottom edge of the sheet, there are two assemblies of strips 330 and 331 of web-like material positioned in-line. Each assembly contains a D-ring attached to a strip of web-like material attached to the matrix sheet and further having length of web-like material having Velcro layers attached thereto in line with the D-ring. The said length of web-like material extends through the D-ring and loops back onto itself, and is secured together via the Velcro. These assemblies serve to store and secure different sizes of items having a central orifice through which the strap can be inserted such as a roll of tape.

The dynamic aspect of the portable medical equipment pack of the present invention is that there is a collection of different sized removable pouches that are secured to the interior side of the portable medical equipment pack via Velcro means. The pouches store equipment therein, preferably medical equipment.

As depicted in FIG. 4, the portable medical equipment pack 401 is suspended from a wall surface that is not vertical using top assemblies 407 and 408, said assemblies being located and extending diagonally inward at a 45° angle from the top two apexes. The assemblies secure the portable medical equipment pack to the angular or arcuate wall of the shelter.

Bottom assemblies 409 and 410 serve to hold the portable medical equipment pack 401 against the surface of the supporting structure.

In the preferred embodiment of the invention, there are eight pouches arranged in columns and rows that are secure via Velcro, or some other suitable fastening means to the interior of portable medical equipment pack 401. Starting from the top of the portable medical equipment pack as depicted in FIG. 4, two of the pouches 440 and 441 located abreast of each other are clear removable pouches made from a vinyl plastic with zippers and measure about 14"W×5"H× 3"thick.

Beneath those two pouches, there are two more pouches 442, 443, (two abreast) that are clear removable pouches made from a vinyl plastic with zippers and measure about 14"W×9"H×3"thick.

Beneath pouches 442 and 443, there are two more pouches 444, 445, (two abreast) that are clear removable pouches made from a vinyl plastic At the bottom of the portable medical equipment pack 401, there are two clear removable vinyl pouches 446 and 447 that measure 15"×15", fold over on each other and include compartments sewn stitched therein to hold smaller medical supplies.

Each of the various pouches described above has a clear sewn-in compartment or slot in its front to contain labels to be inserted therein to provide a quick visual list and inventory of contents. All of the removable pouches can contain medical supplies such as bandages, IV bags, and masks, and associated medical equipment.

The area of the portable medical equipment pack depicted in FIG. 4 is approximately 1520 in$^2$ (approximately 1 meter$^2$). The dimension of the storage pack has significance because the storage pack is designed (inter alfa) to hang on the wall of the type of deployable shelter disclosed in U.S. patent application Ser. No. 12/322,062 to A. Jon Prusmack, the contents of which are hereby incorporated by reference herein. The shelters described in the aforementioned application comprise a frame formed from square quads having hubs at each apex of the quad and in the center thereof. The interior fabric wall of the shelter is held in place by keepers which screw into the hubs forming the frame. Each of these keepers has a loop extending out therefrom. The loops serve as means to connect the web straps of assemblies 407, 408, 409 and 410 to the shelter.

The dimension of the sheet (preferably between 39"×39" 40"×40" and 40"×38") is designed to allow the sheet, using the one inch heavy weight adjustable web straps 407, 408, 409 and 410 with quick release buckles sewn on all four corners of the sheet, to be attached to the loops extending from the keepers (not shown) thereby hanging the storage pack on the interior wall of the shelter. The center of the portable medical equipment pack contains a grommet (not shown, 312 in FIG. 3) which aligns with the central hub located in the center of the square quads noted above. A keeper (not shown) is inserted through the grommet and screwed into the central hub in the quad and the portable medical equipment pack is held taut against the interior wall of the shelter.

On a first side of the portable medical equipment pack depicted in FIG. 4, adjacent to and in between Velcro strip 419 on the edge of the portable medical equipment pack and the column of pouches 440, 442, 444, and 446 depicted, there is a column of expandable elastic loops 422, 423, 424 and 425. FIG. 4 shows a cylindrical item held within loops 423 and 425, whereas loops 422 and 424 have no items within.

At the bottom of portable medical equipment pack 401, and parallel to Velcro strip 421 that extends along the bottom edge of portable medical equipment pack 401, there are two assemblies of strips 430 and 431 of web-like material positioned in-line. Each assembly contains a D-ring attached to a strip of web-like material attached to the matrix sheet and further having length of web-like material having Velcro layers attached thereto in line with the D-ring. Assembly 430 is depicted storing as a roll of tape.

Some of the eight pouches depicted in FIG. 4, by way of illustration, show items contained within the pouches. Pouches 444 and 445 show items secured by elastic bands 450 and 451 sewn to the front surface thereof.

As noted FIG. 4 depicts the preferred embodiment of the present invention as being designed to hang on the interior wall of the deployable shelter mentioned above which shelter serves as an emergency room, ICU, triage area, etc.

Figure 5:
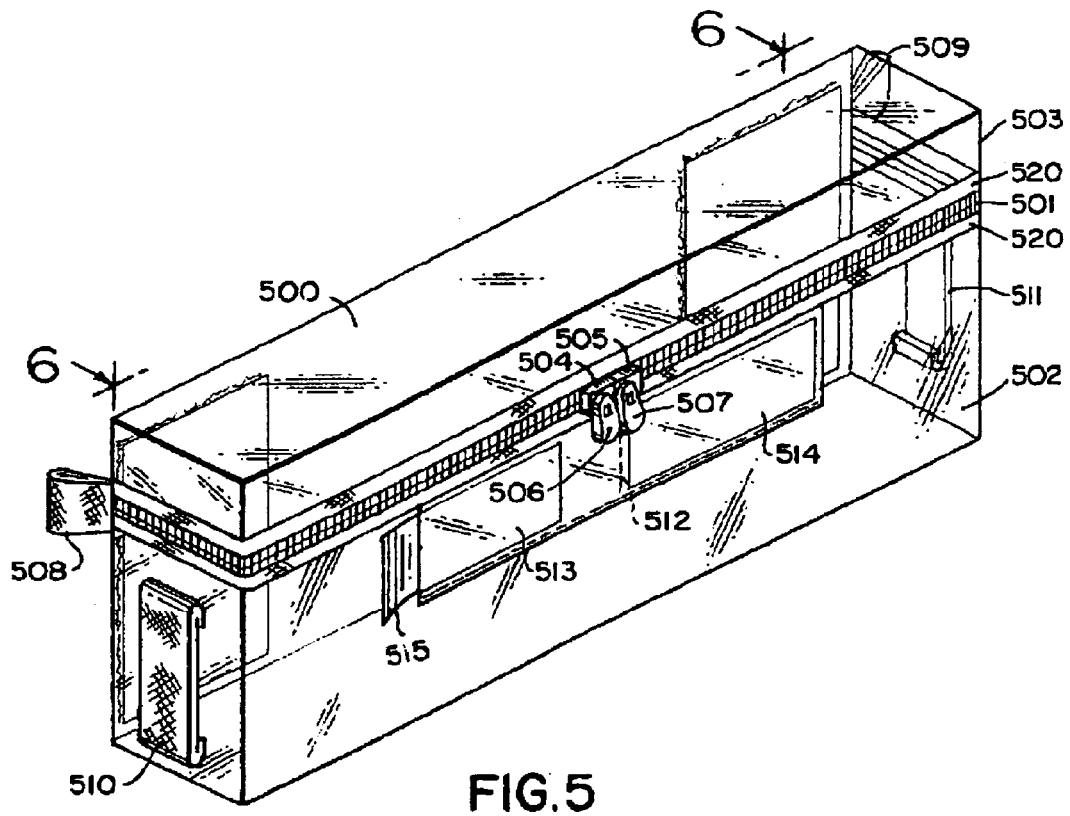
FIG. 5 is an orthogonal view of one of the smaller pouches contained within the interior of the portable medical equipment pack of the present invention.

FIG. 5 depicts one of the pouches located at the top of the collection of pouches in the portable medical equipment pack. The pouch 500 is depicted in FIG. 4, as either of pouches 440 or 441 located abreast of each other.

FIG. 5 is an isometric view of pouch 500. Pouch 500 is a removable pouch, measuring about 14"W×5"H×3"thick, preferably made from a clear vinyl plastic, or the like, with a zipper 501 that separates and connects a bottom section 502 from a top section 503. Zipper 501 is a chain comprising the continuous piece that is formed when the teeth secured to the bottom of section 502 and the teeth secured to the top of section 503 are meshed together to secure top section 502 to bottom section 503. Zipper 501 contains one or two sliders 504, 505, i.e., a device that moves along the chain to open or close the zipper, each with a pull tab 506, 507 used to hold or move the slider.

Each side of zipper 501 is secured to fabric tape (as detailed in the description relating to FIG. 7) which is in turn secured to the plastic material forming the pouch. Zipper 501 extends along the entire depth (sides) and width (front) dimensions of the pouch. Zipper 501 does not extend along the rear side of the pouch.

At the back edge of pouch 500 at each side, there are finger tabs 508 and 509 which are used as grips to remove the pouch from the Velcro back to which it is attached when in storage or transit. Along each side of the pouch there are web straps 510 and 511 which can be used as a handle to carry the pouch when removed from the portable medical equipment pack. In the front of pouch 501 is an open-ended bifurcated compartment 512 comprising two sections 513 and 514 which serve to contain cards that list by printing, drawing or otherwise, the contents contained within the individual pouch. FIG. 5 depicts a card 515 adapted to disclose the contents of the pouch partially inserted into one section 513 of compartment 512.

Figure 6:
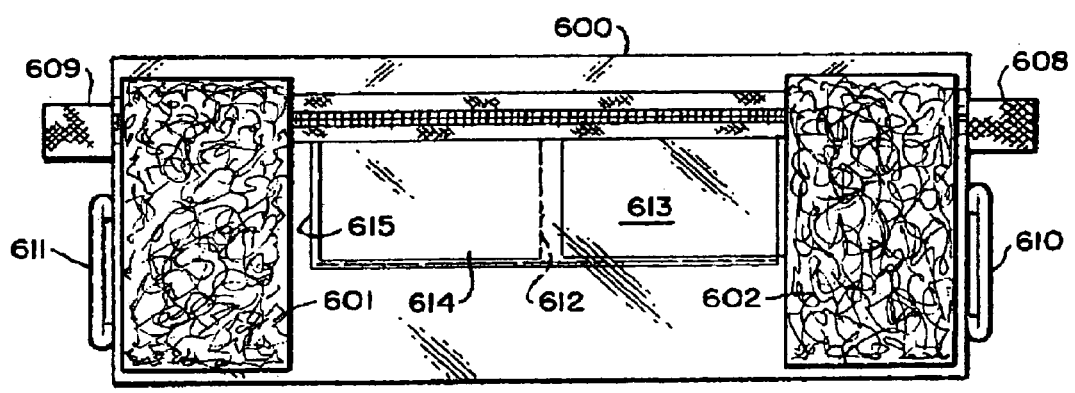
FIG. 6 is a rear view of the smaller pouch depicted in FIG. 5.

FIG. 6 is a rear view of the pouch depicted in FIG. 5. FIG. 6 shows the rear of pouch 600 with Velcro strips 601 and 602 which together with the Velcro strips secured to the interior side of the portable medical equipment pack, hold the pouch securely in place in storage and/or use.

FIG. 6 also shows tabs 608 and 609 and web straps 610 and 611 located at the side of the pouch. Looking through the back of the pouch to the front thereof, compartment 612 at the front of the pouch has a dividing seam that separates bifurcated compartment 612 into sections 613 and 614. An index card 615 is shown partially inserted into section 614. Index card 615 contains a written description of the contents contained within the pouch and the description of same is visible from the front of the pouch when pouch 600 is adhered to the Velcro strips situated on the interior side of the portable medical equipment pack as depicted in FIG. 3.

FIG. 7 depicts pouch 700 which is one of two pouches situated abreast each other in of the collection of pouches in the portable medical equipment pack. Pouch 700 is located directly beneath pouch 500 depicted in FIG. 5 and described above. The pouch 700 is depicted in FIG. 4, as either of pouches 440 or 441 located abreast of each other.

FIG. 7 is an orthogonal view of pouch 700. Pouch 700 is a removable pouch, measuring about 14"W×9"H×3"thick, preferably made from a clear vinyl plastic, or the like, with a zipper 701 that separates and connects a bottom section 702 from a top section 703. Zipper 701 is a chain comprising the continuous piece that is formed when the teeth secured to bottom section 702 and the teeth secured to top section 703 are meshed together to secure top section 702 to bottom section 703. Zipper 701 contains one or two sliders 704, 705, i.e., a device that moves along the chain to open or close the zipper, each with a pull tab 706, 707 used to hold or move the slider.

The teeth on each side of zipper 701 is secured to fabric tape 720 which is in turn secured to the material forming the pouch. Zipper 701 extends along the entire depth (sides) and width (front) dimensions of the pouch. Zipper 701 does not extend along the rear side of the pouch.

At the back edge of pouch 700 at each side, there are finger tabs 708 and 709 which can be used as grips to remove the pouch from the Velcro strips located on the interior surface of the portable medical equipment pack to which pouch 700 is attached when in storage or transit. Along each side of pouch 700 there are web straps 710 and 711 which can be used as a handle to carry the pouch when removed from the portable medical equipment pack. In the front of pouch 701 is an open-ended bifurcated compartment 712 comprising two sections 713 and 714 which serve to contain cards that list by printing or otherwise, the contents contained within the pouch. FIG. 7 contains a card in sections 713 and 714 which serve to disclose the contents of the pouch.

The front face of pouch 700 contains a flexible elastic band that is stitched to the face of pouch 700 to form segments 723, 724, 725, 726 and 727 which are designed to hold equipment used by the personnel using the portable medical equipment pack at the emergency site. Segments 723 and 725 illustrate how items are stored in the segments of the flexible elastic band.

Figure 7A:
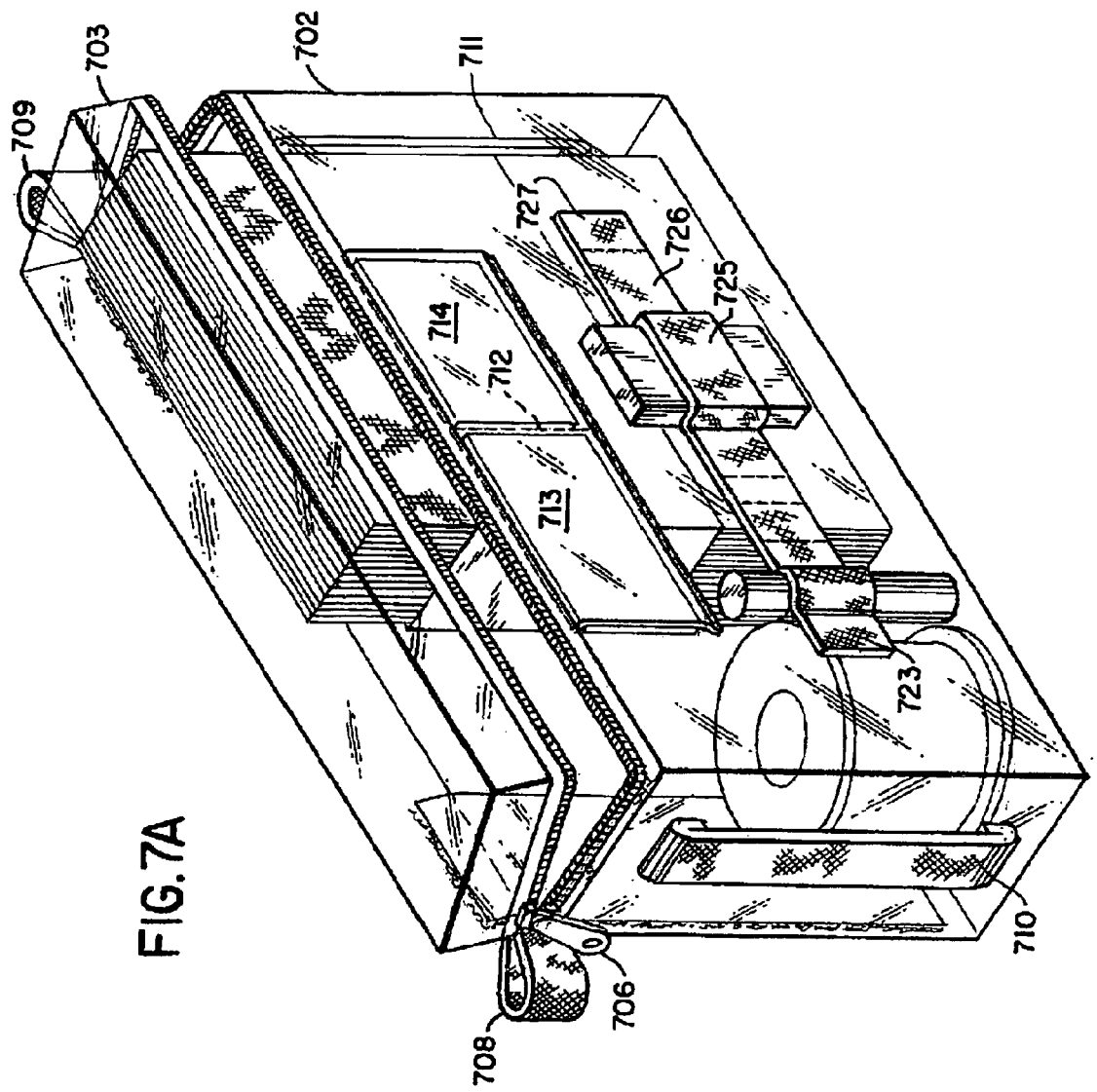
FIG. 7A is an orthogonal view of one of the larger pouches contained within the interior of the portable medical equipment pack of the present invention with its top portion open.

FIG. 7A depicts the pouch described in FIG. 7 above with the same elements, except that the zipper via pull tab 706 has opened the pouch. Thus sections 702 and 703 are not joined by the zipper and the user has access to the contents within the pouch.

FIG. 8 is a rear view of pouch 700 depicted in FIG. 7. FIG. 8 shows the rear of pouch 800 with Velcro strips 801 and 802 which together with the Velcro strips secured to the interior side of the portable medical equipment pack, hold the pouch securely in place in storage and/or use.

FIG. 8 also shows the tabs 708 and 709 as described in FIG. 7 and web straps 810 and 811 located at the side of the pouch. Looking through the back of pouch 800 to the front thereof, compartment 812 at the front of the pouch has a dividing seam 812' that separates bifurcated compartment 812 into sections 813 and 814. Labeling cards 813 and 814 are inserted into section 812.

Figure 9:
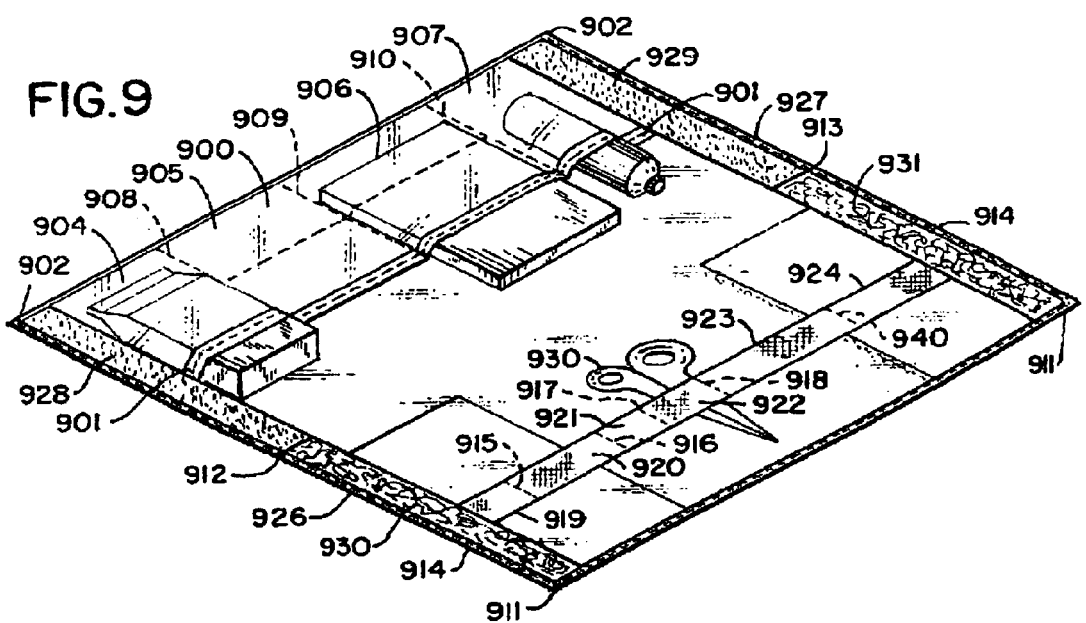
FIG. 9 is an isometric view of one of the overlap pouches contained within the interior of the portable medical equipment pack of the present invention.

FIG. 9 depicts a perspective view of the last type of pouch found in the portable medical equipment pack of the present invention. The pouch assembly has an interior pocket and a closure flap that folds down over the front to cover the pocket. FIG. 9 depicts the interior of pouch 900.

The pouch assembly of the present invention is formed initially from a flat rectangular sheet of transparent vinyl or similar clear flexible plastic material. The plastic forming the overlapping envelope pouch is supple enough to facilitate folding horizontally along two preselected lines so that a three part fold-over pouch is obtained.

As noted above, pouch 900 is formed from a flat rectangular sheet which has an exterior surface, an interior surface, a bottom edge, a top edge and two sides comprising a right and a left side. To form pouch 900 as used in the present invention, the initial bottom edge 901 of the rectangular sheet from which the pouch is formed is folded up on itself so that edge 901 is then located substantially as shown in FIG. 9. The resultant bottom edge of the pouch after folding up on itself is a folded crease 902 which extends horizontally along the bottom width of the pouch. Folded crease 902 then becomes the bottom of the pouch and initial bottom edge after folding up on itself becomes the top edge of pocket 903. The contiguous edges along each of its right and left sides (not shown) resulting from the fold-over are sealed together, thus forming a pocket within the horizontal width of the pouch from top to bottom of same. The pocket covering the width of the pouch is divided into a series of smaller pockets 904, 905, 906 and 907 in which items needed for emergency treatment are stored. The smaller pockets 904, 905, 906 and 907 are formed by vertically stitching together the front of the pocket to the back of pocket at a plurality of parallel locations 908, 909 and 910, said lines of stitching extending from the folded crease 902 formed at the bottom of the pouch up to the top 901 of the newly formed pocket.

The remainder of the flat rectangular sheet extending from the top 901 of the formed pocket to the top edge 911 of the sheet is then available for folding over along a plane extending between points 912 and 913 which are located substantially half the distance between bottom 902 and top 911 at the top of pouch 900. This area which available to fold over the pocket forms the closure flap depicted in FIG. 10. The result is a pouch that has the general configuration of a fold-over wallet.

A suitable distance beneath the top edge 911, a strip of elastic tape (essentially a band) 914 extending horizontally across the width of the interior of the pouch 900, is sewn into the sheet material. Vertical stitches 915, 916, 917 and 918 are sewn into the band to form individual sections 919, 920, 921, 922, 923 and 924 which are used to secure and store items needed for emergency treatment. Scissors 926 are shown being held in place by the flexible elastic band in section 922.

Extending along each interior left and right side edge 926 and 927 of the pouch there is a pair of mating Velcro strips 928, 929 and 930 and 931. These Velcro strips used in pouch 900 are divided into two mating parts. The first Velcro strips 928 and 929 each possess a surface with hooks. The second Velcro strips 930 and 931 each possess a surface of loops. Thus when the top half of the front section or closure flap is folded over on itself, the Velcro strips provide a secure interior portion such that items contained within the interior of the pouch will not be lost.

Figure 10:
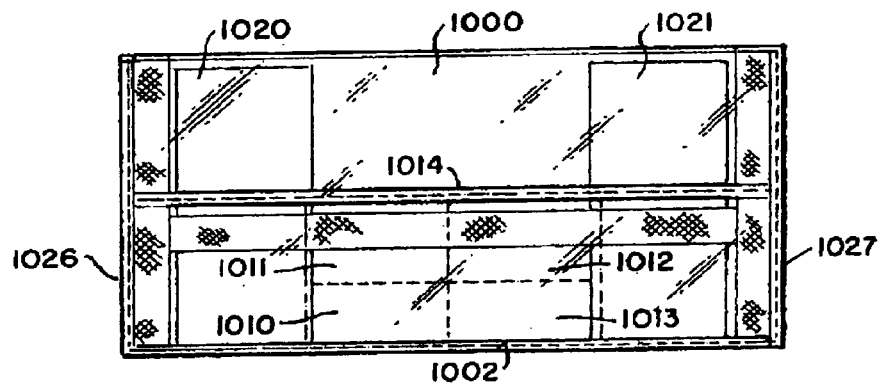
FIG. 10 is a front view of the overlap pouch depicted in FIG. 9 in its folded state.

FIG. 10 depicts the front of the closure flap 1001 of pouch 1000. On the front face of the closure flap 1001 there are four pockets 1010, 1011, 1012 and 1013 defined by stitching a piece of transparent plastic to the front of closure flap 1001 and dividing it into compartments of 2 rows and 2 columns. The compartments are used to contain cards having a description of the contents of the pouch. Edges 1026 and 1027 show the hidden location of the Velcro strips which hold the body of the pouch to closure flap 1001. The location of the strip of elastic tape (essentially a band) 1014 extending horizontally across the width of the interior of pouch 1000, is shown in FIG. 10. The front of Velcro strips 1020 and 1021 which mate up with the Velcro strips in the interior of the portable portable medical equipment pack are visible through the front of the pouch.

Figure 11:
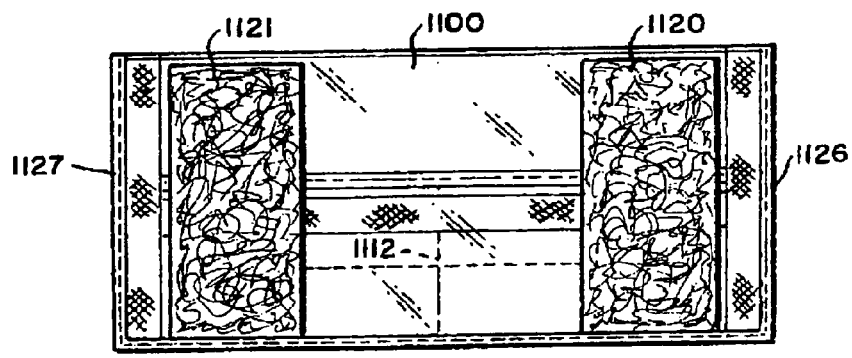
FIG. 11 is a rear view of the overlap pouch depicted in FIG. 9 in its folded state. portable medical equipment pack

FIG. 11 depicts the back of pouch 1100 showing Velcro strips 1120 and 1121, the four compartments 1110, 1111, 1112 and 1113, the location of the band of elastic tape 1114 and the edges 1126 and 1127 which is the hidden location of the Velcro strips which hold the body of the pouch to the closure flap.

The foregoing discussion of the various aspects of invention has been presented for purposes of illustration and description. The foregoing is not intended to be exhaustive or to limit the invention to the precise form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. Where specific "means" are described in the specification for the purpose of illustration, the description given is by way of illustration and not by way of limitation. For example when, referring to stitching to form or hold together, any suitable means of securing one piece to another may conveniently be used. Such modifications and variations that may be apparent to a person skilled in the art are intended to be included within the scope of the invention as defined by the accompanying claims. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What we claim and desire to protect by Letters Patent is:

1. A portable pack for storing supplies and equipment comprising:
    a rectangular sheet of flexible polymeric material impervious to water, inorganic and organic compounds, said sheet capable of being folding in half;
    said sheet having:
    an exterior side, an interior side, a top edge, a bottom edge, a left side and a right side;
    and having a grommet positioned substantially in the center of said sheet when folded in half with an opening in said grommet extending through said sheet from said exterior side to said interior side through which a fastener may be passed;
    said interior side of said sheet having secured thereto:
    a first alignment of first fastening means positioned at the peripheral edge of and extending continuously along said bottom edge, said left side and said right side;
    a second alignment of second fastening means positioned adjacent and parallel to one other and extending vertically between said bottom edge and said top edge;
    a row comprising plurality of expandable loops secured to said sheet in vertical alignment with one another positioned on said left side and said right side and adjacent on said sheet to said first alignment of fastening means extending continuously along said left side and said right side;
    a pair of two-piece cooperating strap assemblies, in horizontal alignment with each other and extending parallel to and adjacent on said sheet to said alignment of said first fastening means extending continuously along said bottom edge, each said assembly comprising an alignment of fastening means material having a first end secured to said sheet and second end which is free to be inserted through a D-ring and looped back on itself, said D-ring being attached to a strip secured to said sheet, said assembly serving to secure objects;
    located and positioned diagonally inward at a 45° angle from each apex of the corners of said sheet is an assembly comprising a quick release buckle and a strip of a web-like material, said quick release buckle adapted to adjustably secure extremities of said web-like material including a frame-like body portion, a through slot formed in a trailing end section of said body portion for fixedly securing said buckle to one extremity of said web-like material and means for adjusting the opposite extremity of said web-like material including at least two transverse parallel bars positioned adjacent the opposite end of said body portion, said adjusting means including two transverse parallel bars providing edges spaced from one another on opposite sides of a plane a distance not greater than the predetermined thickness of said web and lying in spaced planes perpendicular to said first mentioned plane;
    two assemblies comprising strips of web-like material positioned in-line and immediately adjacent said fastening means along the bottom edge of said sheet, each said assembly containing a D-ring attached to a strip of web-like material attached to said sheet and a counterpart length of web-like material having a fastener attached thereto in line with the D-ring, in each case, said length of web-like material extends through the D-ring and loops back onto itself, and is secured together via said fastener;
    a plurality of flexible pouches arranged in-line horizontally and vertically and removably secured to said interior sheet, said pouches being suitable for storing items within, each said pouch having a backside with fastening means attached thereto which allows said pouch to be secured to said interior to at least one of the plurality of fastening means positioned adjacent and parallel to one other and extending vertically between said top edge and said bottom edge of said sheet;
    said exterior surface of said material has a continuous support strap secured thereto, and at each end of said pack said continuous strap extends beyond said top and bottom edges of said exterior surface to form a handle and carrying means at each end of said pack, and one of said handles has a handle wrap to secures both ends of said handle wraps into said handle wrap.

2. A portable pack for storing supplies and equipment comprising:
- a rectangular sheet of flexible polymeric material impervious to water, inorganic and organic compounds, said sheet capable of being folding in half;
- said of flexible polymeric material sheet having:
- an exterior side, an interior side, a top edge, a bottom edge, a left side and a right side;
- and having a grommet positioned substantially in the center of said sheet when folded in half with an opening in said grommet extending through said sheet from said exterior side to said interior side through which a fastener may be passed;
- said interior side of said sheet having secured thereto:
  a.) a border strip of hook and loop positioned at the peripheral edge of and extending continuously along, said left side, said bottom edge and said right side;
  b.) a plurality of interior hook and loop strips positioned adjacent and parallel to one another and extending vertically between said top edge and said bottom edge;
  c.) two columns containing a plurality of expandable loops secured to said sheet in vertical alignment with one another, one said column positioned on said left side and one said column on said right side, each said column being adjacent on said sheet to said border hook and loop strip extending continuously along said left side and said right side;
  d.) a pair of two-piece cooperating strap assemblies, in horizontal alignment with each other and extending parallel to and adjacent on said sheet to said border hook and loop strip extending continuously along said bottom edge, each said strap assembly comprising a strip of hook and loop material thereon having a first end secured to said sheet and second end which is free to be inserted through a D-ring and looped back on itself, said D-ring being attached to a strip secured to said sheet, said assembly serving to secure objects;
  e.) an assembly comprising a quick release buckle and a strip of a web-like material, said assembly located and positioned diagonally inward at a 45° angle from each apex of the corners of said sheet, said quick release buckle being adapted to adjustably secure extremities of said web-like material including a frame-like body portion, fastening means at one end of said body portion for fixedly securing the buckle to one extremity of said web-like material and means for adjusting the opposite extremity of said web-like material including at least two transverse parallel bars positioned adjacent the opposite end of said body portion, said adjusting means including two transverse parallel bars providing edges spaced from one another on opposite sides of a plane a distance not greater than the predetermined thickness of said web and lying in spaced planes perpendicular to said first mentioned plane;
- two assemblies comprising strips of web-like material positioned in-line and immediately adjacent said hook and loop along the bottom edge of said sheet, each said assembly containing a D-ring attached to a strip of web-like material attached to said sheet and a counterpart length of web-like material having hook and loop layers attached thereto in line with the D-ring, in each case, said length of web-like material extends through the D-ring and loops back onto itself, and is secured together via said hook and loop;
- a plurality of flexible pouches arranged in-line horizontally and vertically and removably secured to said interior sheet, said pouches being suitable for storing items within, each said pouch having a backside with hook and loop attached thereto which allows said pouch to be secured to said interior to at least one of the plurality of hook and loop strips positioned adjacent and parallel to one other and extending vertically between said top edge and said bottom edge of said sheet;
- said exterior surface of said material has a continuous support strap secured thereto, and at each end of said pack said continuous strap extends beyond said top and bottom edges of said exterior surface to form a handle and carrying means at each end of said pack, and one of said handles has a handle wrap to secures both ends of said handle wraps into said handle wrap.

3. The portable pack defined in claim 2 which is used as a portable medical emergency equipment pack having horizontal and vertical sides measuring between about 39 inches and 41 inches.

4. The portable pack defined in claim 3 wherein said rectangular sheet is formed from a high performance nylon 6,6 material.

5. The portable pack defined in claim 4 wherein said pack is carried folded in half and said handles at each end of said pack, are placed in contact with each other and are secured within said handle wrap.

6. The portable pack defined in claim 5 wherein there are at least eight clear vinyl pouches secured via hook and loop to said interior of said pack.

7. The portable pack defined in claim 6 wherein there are four rows and 2 columns of pouches, wherein a first row has two pouches abreast measuring 14×5×3 inches, a second row and a third row which each have two pouches abreast measuring 14×9×3 inches, and a fourth row having two pouches abreast measuring 15×15 inches folded over on each other each of which includes compartments sewn stitched therein to hold small supplies.

8. The portable pack defined in claim 6 wherein each said pouch positioned in said first, second and third rows has an opening across the top thereof which are opened and closed by a zipper.

* * * * *